US00PP28315P2

(12) United States Plant Patent
Hofmann

(10) Patent No.: US PP28,315 P2
(45) Date of Patent: Aug. 22, 2017

(54) ***MANDEVILLA* PLANT NAMED 'INMANREDSCAR'**

(50) Latin Name: ***Mandevilla* hybrid**
Varietal Denomination: INMANREDSCAR

(71) Applicant: Birgit Hofmann, Rudesheim am Rhein (DE)

(72) Inventor: Birgit Hofmann, Rudesheim am Rhein (DE)

(73) Assignee: InnovaPlant GMBH & Co. KG, Gensingen (DE)

( * ) Notice: Subject to any disclaimer, the term of this patent is extended or adjusted under 35 U.S.C. 154(b) by 11 days.

(21) Appl. No.: 14/998,801

(22) Filed: Feb. 17, 2016

(51) Int. Cl.
*A01H 5/02* (2006.01)

(52) U.S. Cl.
USPC ..... Plt./232

(58) Field of Classification Search
USPC ..... Plt./232
See application file for complete search history.

*Primary Examiner* — Keith Robinson

(57) ABSTRACT

A new cultivar of *Mandevilla* plant named 'INMANREDSCAR' that is characterized by early flowering, a compact habit, green leaves and large red flowers that open wide and are resistant to sun fading.

1 Drawing Sheet

Botanical classification: *Mandevilla* hybrid.
Variety denomination: 'INMANREDSCAR'.

BACKGROUND OF THE INVENTION

The present invention relates to a new and distinct cultivar of *Mandevilla* plant botanically known as *Mandevilla* hybrid and hereinafter referred to by the cultivar name 'INMANREDSCAR'.

The new *Mandevilla* is the product of a planned breeding program conducted by the inventor in Gensingen, Germany. The objective of the breeding program is to create new *Mandevilla* cultivars that flower early and have large flowers that do not fade with sun exposure.

'INMANREDSCAR' originated from a crossing in 2008 of the female or seed parent *Mandevilla* 'Rio White' (not patented) and the male or pollen parent *Mandeville*. 'Rio Pink' (not patented). The resulting seeds were subsequently planted and grown. The cultivar 'INMANREDSCAR' was selected by the inventor in 2009 as a single plant within the progeny of the stated cross in Gensingen, Germany.

Asexual reproduction of the new cultivar 'INMANREDSCAR' first occurred by terminal cuttings in 2009 in Gensingen, Germany. Since that time, under careful observation, the unique characteristics of the new cultivar have been uniform, stable and reproduced true to type in successive generations of asexual reproduction.

SUMMARY OF THE INVENTION

The following represent the distinguishing characteristics of the new *Mandevilla* cultivar 'INMANREDSCAR'. These traits in combination distinguish 'INMANREDSCAR' as a new and distinct cultivar apart from other existing known varieties of *Mandevilla*.

1. *Mandevilla* 'INMANREDSCAR' exhibits early flowering.
2. *Mandevilla* 'INMANREDSCAR' exhibits a compact habit.

3. *Mandevilla* 'INMANREDSCAR' exhibits green leaves.
4. *Mandevilla* 'INMANREDSCAR' exhibits large red flowers that open wide.
5. *Mandevilla* 'INMANREDSCAR' exhibits flowers that are resistant to sun fading.

The closest comparison cultivars are *Mandevilla* 'Sundaville Red' (not patented) and *Mandevilla* 'Rio Red' (not patented).

'INMANREDSCAR' is distinguishable from 'Sundaville Red' by the following characteristics:

1. 'INMANREDSCAR' exhibits earlier flowering than 'Sundaville Red'.
2. 'INMANREDSCAR' exhibits a more compact habit with less climbing than 'Sundaville Red'.
3. 'INMANREDSCAR' has wider leaves that are lighter green in color than the leaves of 'Sundaville Red'.
4. 'INMANREDSCAR' exhibits larger flowers that open wider and that are lighter red in color than the flowers of 'Sundaville Red'.
5. 'INMANREDSCAR' exhibits flowers that are more resistant to sun fade than the flowers of 'Sundaville Red'.

'INMANREDSCAR' is distinguishable from 'Rio Red' by the following characteristics:

1. 'INMANREDSCAR' exhibits earlier flowering than 'Rio Red'.
2. 'INMANREDSCAR' exhibits larger flowers that open wider and are that are lighter red in color than the flowers of 'Rio Red'.
3. 'INMANREDSCAR' exhibits flowers that are more resistant to sun fade than the flowers of 'Rio Red'.
4. 'INMANREDSCAR' exhibits a faster rooting time than 'Rio Red'.

'INMANREDSCAR' is distinguishable from the female parent 'Rio White' by the following characteristics:

1. 'INMANREDSCAR' exhibits earlier flowering than 'Rio White'.
2. 'INMANREDSCAR' exhibits a more compact habit than 'Rio White'.

3. 'INMANREDSCAR' exhibits larger flowers than the flowers of 'Rio White'.
4. 'INMANREDSCAR' exhibits red flowers. In contrast, the flowers of 'Rio White' are white.
5. 'INMANREDSCAR' exhibits leaves that are shorter than. the leaves of 'Rio White'.

'INMANREDSCAR' is distinguishable from the male parent 'Rio Pink' by the following characteristics:

1. 'INMANREDSCAR' exhibits larger flowers than the flowers of 'Rio Pink'.
2. 'INMANREDSCAR' exhibits red flowers. In contrast, the flowers of 'Rio Pink' are pink.
3. 'INMANREDSCAR' exhibits lighter green leaves than the leaves of 'Rio Pink'.
4. 'INMANREDSCAR' exhibits leaves that are wider than the leaves of 'Rio Pink'.

BRIEF DESCRIPTION OF THE DRAWING

The accompanying photograph illustrates the distinguishing traits of *Mandevilla* 'INMANREDSCAR'. The plant in the photograph shows an overall view of an 8 month old plant. The photograph was taken using conventional techniques and although colors may appear different from actual colors due to light reflectance it is as accurate as possible by conventional photographic techniques.

BOTANICAL DESCRIPTION OF THE PLANT

The following is a detailed description of the new *Mandevilla* cultivar named 'INMANREDSCAR'. Data was collected in Gensingen, Germany from 8 month old glass greenhouse grown plants in 16 cm. diameter containers. The time of year was Summer and the temperature range was 15-28 degrees Centigrade during the day and 8-20 degrees Centigrade at night. No growth retardants were used. Color determinations are in accordance with The Royal Horticultural Society Colour Chart 2007 edition, except where general color terms of ordinary dictionary significance are used. The growing requirements are similar to the species. 'INMANREDSCAR' has not been tested under all possible conditions and phenotypic differences may be observed with variations in environmental, climatic, and cultural conditions, however, without any variance in genotype.

Botanical classification: *Mandevilla* hybrid 'INMANREDSCAR'.
Annual or perennial: Annual.
Parentage: 'INMANREDSCAR' is the product of the female or seed parent *Mandevilla* 'Rio White' and the male or pollen parent *Mandevilla* 'Rio Pink'.
Vigor: Moderate.
Growth habit Vining.
Plant shape: Upright.
Suitable container size: 14-18 cm.
Height: 30 cm. in height.
Diameter: 20 cm. in diameter.
Low temperature tolerance: 5° Centigrade.
High temperature tolerance: 35° Centigrade.
Propagation: Terminal cuttings.
Time to initiate roots in summer: 25 days to initiate roots at 24° Centigrade.
Time to initiate roots in winter: 25 days to initiate roots at 24° Centigrade.
Time to produce a rooted cutting or liner in summer: 25 days at 24° Centigrade.
Time to produce a rooted cutting or liner in winter: 25 days at 24° Centigrade.
Crop time: Approximately 3 to 4 months.
Root system: Thick and fleshy.
Root color: N155.
Stem:
*Branching habit.*—Freely branching.
*Basal branching.*—Yes.
*Average number of lateral branches.*—20.
*Pinching.*—One pinch after planting.
*Lateral branch dimensions.*—2.75 mm. in diameter and 15 cm. in length.
*Internode length.*—3 cm.
*Stem texture.*—Smooth.
*Stem strength.*—Strong.
*Stem color.*—144A.
*Pubescence.*—Absent.
Foliage:
*Leaf arrangement.*—Opposite.
*Compound or single.*—Single.
*Number of leaves per lateral branch.*—33.
*Leaf shape.*—Ovate.
*Leaf apex.*—Cuspidate.
*Leaf base.*—Obtuse.
*Leaf dimensions.*—6 cm. in length and 3.8 cm. in width.
*Texture.*—Glabrous on both surfaces.
*Pubescence.*—None.
*Leaf margin.*—Entire.
*Venation pattern.*—Pinnate.
*Young leaf color (upper surface).*—146A.
*Young leaf color (lower surface).*—144A.
*Mature leaf color (upper surface).*—146A.
*Mature leaf color (lower surface).*—144A.
*Vein color (upper surface).*—144C.
*Vein color (under surface).*—144D.
*Petiole dimensions.*—1.25 cm. in length and 2 mm. in diameter.
*Petiole color.*—144D.
*Durability of foliage to stress.*—High.
Flower:
*Inflorescence arrangement.*—Single salverform flowers arranged in axillary racemes.
*Inflorescence dimensions.*—10 cm. in height and 10 cm. in width.
*Quantity of flowers per inflorescence.*—3 to 4.
*Flower type.*—Salverform, flared trumpet, corolla fused and five-parted.
*Quantity of flowers per lateral stem.*—12.
*Quantity of flower buds per lateral stem.*—20.
*Quantity of flowers and buds per plant.*—Average 55.
*Natural flowering season.*—Summer to Late Autumn.
*Time to flower.*—6 weeks.
*Fragrance.*—None.
*Flower bud length.*—8 cm.
*Flower bud diameter.*—1.5 cm.
*Flower bud shape.*—Oblong.
*Bud color.*—155A, tip 51A.
*Rate of bud opening.*—2 to 5 days.
*Flower aspect.*—Outward.
*Flower shape.*—Trumpet shaped.
*Flower dimensions.*—10 cm. in diameter and 7 cm. in height.
*Flower longevity.*—3 to 5 days.
*Number of petals.*—5.
*Fused or unfused.*—Fused.

*Petal arrangement*.—Base fused, flaring outward.
*Petal shape*.—Ovate.
*Petal texture*.—Smooth on both surfaces.
*Petal margin*.—Slightly undulate.
*Petal apex*.—Acuminate.
*Petal base*.—Fused.
*Petal length*.—3.5 cm.
*Petal width*.—3.5 cm.
*Petal color when opening* (*upper side*).—45B.
*Petal color when opening* (*under side*).—53B.
*Petal color fully opened* (*upper side*).—53C with blotches of 45D.
*Petal color fully opened* (*under side*).—52A.
*Petal color fading to*.—53C with blotches of 45D.
*Self-cleaning or persistent*.—Self-cleaning.

Sepals:
*Sepal arrangement*.—Five sepals arranged in a single whorl fused at the base.
*Number of sepals*.—5.
*Sepal shape*.—Lanceolate.
*Sepal margin*.—Entire.
*Sepal apex*.—Acuminate.
*Sepal base*.—Fused.
*Sepal dimensions*.—8 mm. in length and 2 mm. in width.
*Young sepal color* (*upper side*).—150B.
*Young sepal color* (*under side*).—150B.
*Mature sepal color* (*upper side*).—150B.
*Mature sepal color* (*under side*).—150B.

Calyx:
*Calyx shape*.—Funnelform.
*Calyx dimensions*.—8 mm. in length and 4 mm. in diameter.

Peduncle:
*Peduncle dimensions*.—3 cm. in length and 2 mm. in diameter.
*Peduncle angle*.—30 degrees.
*Peduncle strength*.—Strong.
*Peduncle color*.—*N*144B.

Pedicels:
*Pedicel dimensions*.—2.75 cm. in length and 2.5 mm. in diameter.
*Pedicel angle*.—90 degrees.
*Pedicel strength*.—Strong.
*Pedicel color*.—N144B.

Reproduction organs:
*Stamen number*.—5.
*Anther shape*.—Elliptic.
*Anther size*.—8 mm. in length and 2 mm. in width.
*Anther color*.—10B.
*Amount of pollen*.—Low.
*Pollen color*.—10B.
*Pistil number*.—One.
*Pistil length*.—2.5 cm.
*Stigma shape*.—Filiform.
*Stigma color*.—10C.
*Style length*.—2.5 cm.
*Style color*.—10C.
*Ovary color*.—149A.

Fruit and seed: Fruit and seed production has not been observed to date.

Disease and pest resistance: Disease and pest resistance has not been observed to date.

The invention claimed is:

1. A new and distinct variety of *Mandevilla* plant named 'INMANREDSCAR' as described and illustrated.

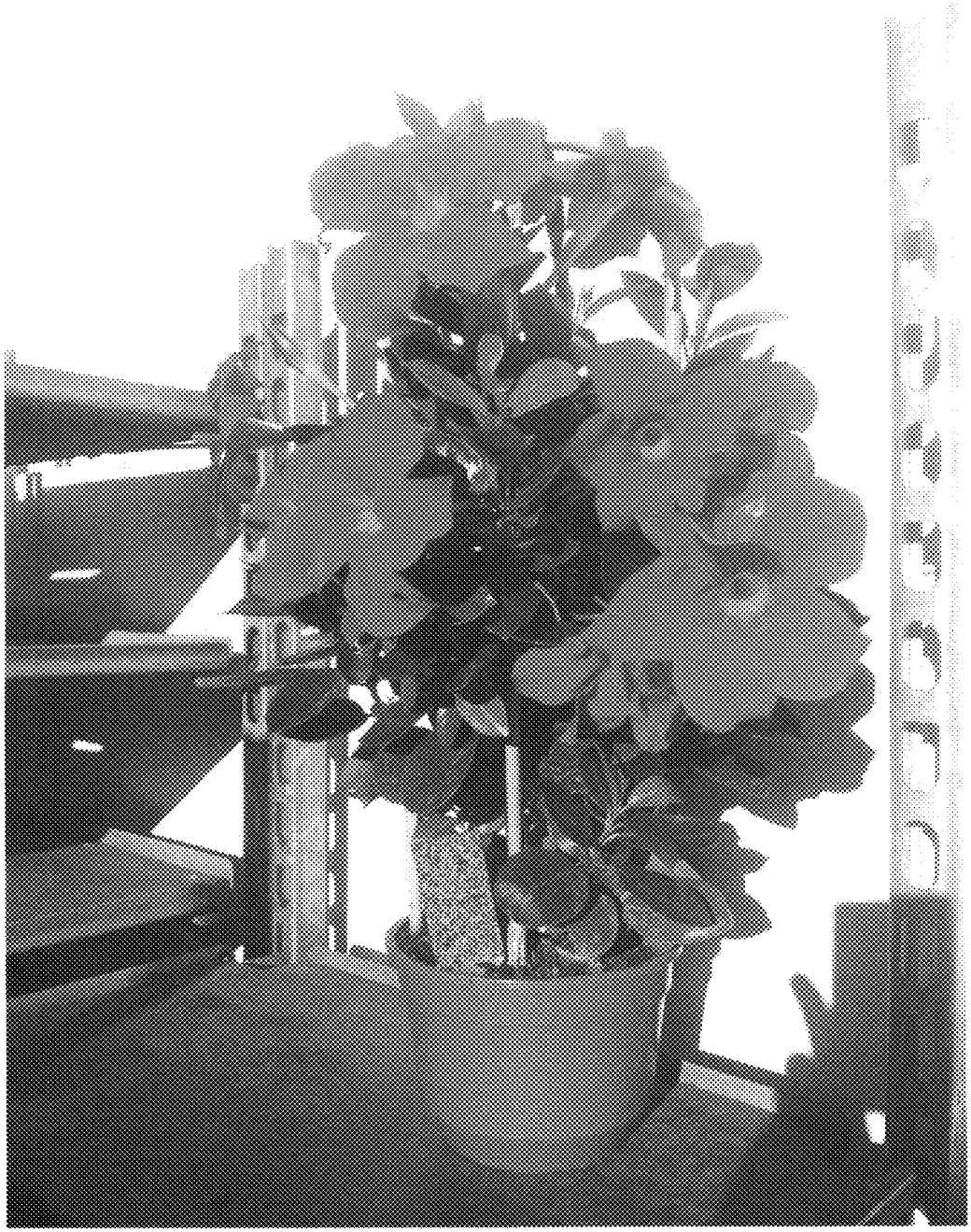

* * * * *